United States Patent
Cinader, Jr. et al.

(10) Patent No.: US 7,726,470 B2
(45) Date of Patent: Jun. 1, 2010

(54) PACKAGED ORTHODONTIC APPLIANCE AND ADHESIVE MATERIAL

(75) Inventors: David K. Cinader, Jr., Walnut, CA (US); Joan V. Brennan, Sierra Madre, CA (US); James D. Christoff, Birchwood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 350 days.

(21) Appl. No.: 11/750,437

(22) Filed: May 18, 2007

(65) Prior Publication Data

US 2008/0286710 A1 Nov. 20, 2008

(51) Int. Cl.
*A61B 19/02* (2006.01)
*B65D 83/10* (2006.01)
*A61C 3/00* (2006.01)

(52) U.S. Cl. ............... 206/63.5; 206/368; 206/369; 433/9

(58) Field of Classification Search ............ 206/63.5, 206/461, 462, 469, 813, 438, 368, 369, 460; 433/8–17, 24
See application file for complete search history.

(56) References Cited

U.S. PATENT DOCUMENTS

| | | | |
|---|---|---|---|
| 3,814,717 A | 6/1974 | Wilson et al. | |
| 4,978,007 A | 12/1990 | Jacobs et al. | |
| 5,015,180 A | 5/1991 | Randklev | |
| 5,152,917 A | 10/1992 | Pieper et al. | |
| 5,172,809 A | 12/1992 | Jacobs et al. | |
| 5,328,363 A | 7/1994 | Chester et al. | |
| 5,429,229 A * | 7/1995 | Chester et al. | ............. 206/63.5 |
| 5,500,273 A | 3/1996 | Holmes et al. | |
| 5,538,129 A * | 7/1996 | Chester et al. | ............. 206/63.5 |
| 5,575,645 A * | 11/1996 | Jacobs et al. | ............ 433/9 |
| 5,636,736 A * | 6/1997 | Jacobs et al. | ............ 206/369 |
| 5,697,780 A | 12/1997 | Tuneberg et al. | |
| 5,759,028 A | 6/1998 | Bozman | |
| 5,762,192 A | 6/1998 | Jacobs et al. | |
| 5,810,582 A | 9/1998 | Doyle et al. | |
| 5,827,058 A * | 10/1998 | Kelly et al. | ............ 433/9 |
| 5,971,754 A | 10/1999 | Sondhi et al. | |
| 6,050,815 A | 4/2000 | Adam et al. | |

(Continued)

FOREIGN PATENT DOCUMENTS

WO  WO 00/69393  11/2000

(Continued)

OTHER PUBLICATIONS

U.S. Appl. No. 09/311,606, filed May 13, 1999 (54867).

(Continued)

*Primary Examiner*—Ehud Gartenberg
*Assistant Examiner*—Dene Quest
(74) *Attorney, Agent, or Firm*—James D. Christoff (57) ABSTRACT

A packaged orthodontic assembly includes a container with a chamber and an orthodontic appliance received in the chamber. A quantity of a first orthodontic adhesive material is applied by the manufacturer to the base of the orthodontic appliance. A second orthodontic adhesive material is also received in the chamber in initially spaced relationship to the first orthodontic adhesive material. The practitioner can elect to bring the first orthodontic adhesive material into contact with the second orthodontic adhesive material when desired.

27 Claims, 5 Drawing Sheets

U.S. PATENT DOCUMENTS

| | | | |
|---|---|---|---|
| 6,089,861 | A | 7/2000 | Kelly et al. |
| 6,126,922 | A | 10/2000 | Rozzi et al. |
| 6,183,249 | B1 | 2/2001 | Brennan et al. |
| 6,213,767 | B1 | 4/2001 | Dixon et al. |
| 6,331,080 | B1 | 12/2001 | Cole et al. |
| 6,444,725 | B1 | 9/2002 | Trom et al. |
| 6,513,897 | B2 | 2/2003 | Tokie |
| 6,528,555 | B1 | 3/2003 | Nikutowski et al. |
| 6,834,761 | B1 | 12/2004 | Kesling |
| 6,843,370 | B2 | 1/2005 | Tuneberg |
| 6,960,079 | B2 | 11/2005 | Brennan et al. |
| 7,188,421 | B2 | 3/2007 | Cleary et al. |
| 2001/0055741 | A1 | 12/2001 | Dixon et al. |
| 2003/0196914 | A1 | 10/2003 | Tzou et al. |
| 2003/0198914 | A1* | 10/2003 | Brennan et al. ............ 433/9 |
| 2005/0175965 | A1 | 8/2005 | Craig et al. |
| 2005/0175966 | A1 | 8/2005 | Falsafi et al. |
| 2005/0176844 | A1 | 8/2005 | Aasen et al. |
| 2005/0205452 | A1* | 9/2005 | Lee et al. ............... 206/484 |
| 2005/0241962 | A1 | 11/2005 | Tuneberg |
| 2006/0054515 | A1* | 3/2006 | Corcoran ............... 206/63.5 |
| 2006/0207893 | A1* | 9/2006 | Cinader et al. .......... 206/63.5 |

FOREIGN PATENT DOCUMENTS

| | | |
|---|---|---|
| WO | WO 2006/058162 | 6/2006 |

OTHER PUBLICATIONS

U.S. Appl. No. 11/425,461, filed Jun. 21, 2006 (62153).
U.S. Appl. No. 11/750,431, filed May 18, 2007 (62053).

* cited by examiner

PACKAGED ORTHODONTIC APPLIANCE AND ADHESIVE MATERIAL

BACKGROUND OF THE INVENTION

1. Field of the Invention

This invention broadly relates to orthodontic appliances and adhesive materials that are applied to a patient's teeth during the course of orthodontic treatment. More particularly, the present invention relates to packaged assemblies that include one or more orthodontic appliances and adhesive materials for use in moving the patient's teeth to desired positions.

2. Description of the Related Art

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth.

In recent years it has become common practice to use adhesives to bond orthodontic appliances to the enamel surfaces of the teeth, using either a direct bonding method or an indirect bonding method. Often, the adhesive is applied to the base of the appliance by the practitioner immediately before the appliance is placed on the tooth. In some instances, a quantity of adhesive is dispensed onto a mixing pad or dispensing well, and a small spatula or other hand instrument is then used to apply a small dab of adhesive to each appliance. In other instances, a quantity of adhesive is dispensed from a syringe directly onto the base of the appliance.

Adhesive precoated brackets are known and offer significant advantages to the orthodontist. Adhesive precoated brackets have a bonding base upon which the manufacturer applies a precise quantity of adhesive, such as a photocurable adhesive. In direct bonding methods, when it is desired to mount an adhesive precoated bracket on a tooth, the bracket is simply removed from the package and placed directly onto the tooth. For indirect bonding methods, brackets are removed from the package and placed, for example, on a replica plaster or "stone" model of the patient's dental arch to provide a custom base for later mounting on the patient's tooth, commonly using a transfer tray or indirect bonding tray.

Adhesive precoated orthodontic appliances are often packaged in containers that protect the adhesive from light, moisture and contaminates. Known containers include containers that receive only a single appliance. The adhesive is coated by the manufacturer onto the base of the appliance and often rests on a release surface within the container. The release surface has properties that facilitate disengagement from the adhesive when the appliance is lifted from the container without unduly disturbing the overall shape of the adhesive.

However, in some instances a practitioner may prefer to use an amount of orthodontic adhesive that is different than the amount of adhesive applied to the base of the appliances by the manufacturer. For example, some practitioners prefer to bond appliances with a relatively small amount of adhesive so that less time is spent removing the adhesive "flash" that extrudes from the base of the appliance as the appliance is pressed onto the tooth surface. Other practitioners, by contrast, prefer to use a larger amount of adhesive when bonding appliances to help ensure that there are no gaps or voids between the base of the appliance and the patient's tooth enamel once the appliance is placed onto the surface of the tooth.

In addition, efforts have long been underway to develop new orthodontic adhesives with improved functional properties. Examples of such properties include sustained fluoride release, moisture tolerance and color-changing characteristics. Unfortunately, the use of some adhesives with conventional orthodontic packaging is not entirely satisfactory because the shelf life of the resultant assembly is relatively short. As can be appreciated, it would be a significant advantage to provide a packaging construction for precoated appliances that can be used with a number of different adhesive materials.

SUMMARY OF THE INVENTION

The present invention is directed toward packaged orthodontic assemblies and related methods, wherein at least one appliance is received in a chamber of a container along with two initially separate quantities of adhesive material. One of the adhesive materials is applied to the base of the appliance by the manufacturer and, when desired, is brought into contact with another adhesive material in the container before the appliance is bonded to the patient's tooth.

In more detail, the present invention in one aspect is directed toward a packaged orthodontic assembly that comprises a container with a chamber and an orthodontic appliance received in the chamber. The appliance includes a base and a first orthodontic adhesive material that extends across the base of the appliance. The assembly also includes a release surface in the chamber and a second orthodontic adhesive material received on the release surface. The second orthodontic adhesive material is spaced in the chamber from the first orthodontic adhesive material.

Another aspect of the present invention is directed toward a method of packaging an orthodontic appliance. The method comprises:

providing an orthodontic appliance and a first orthodontic adhesive material extending across a base of the appliance;

placing a quantity of a second orthodontic adhesive material in a container having a chamber; and supporting the orthodontic appliance in the chamber such that the first orthodontic adhesive material is spaced from the second orthodontic adhesive material.

An additional aspect of the invention is directed toward a method of applying orthodontic adhesive material to an orthodontic appliance. This method comprises:

providing an orthodontic appliance and a first orthodontic adhesive material extending across a base of the appliance;

supporting the orthodontic appliance in a chamber of a container;

placing a second orthodontic adhesive material in the chamber;

closing a cover of the container;

subsequently opening the cover to expose the appliance; and relatively moving the appliance and the second orthodontic adhesive material in the chamber in order to bring the first adhesive material into contact with the second adhesive material.

As one option, the first orthodontic adhesive material is identical to the second orthodontic adhesive material, and the practitioner can elect to bring the first adhesive material into contact with the second adhesive material in instances where an increase in the total amount of adhesive material on the base of the appliance is desired. As another option, the first adhesive material may vary from the second adhesive material in terms of composition, viscosity and/or other characteristics in order, for example, to initiate a chemical reaction and/or enhance the properties of the resultant adhesive composition.

These and other aspects of the invention will be described in more detail below and are illustrated in the accompanying drawings.

DEFINITIONS

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

"Lingual" means in a direction toward the patient's tongue.

DETAILED DESCRIPTION OF THE PREFERRED EMBODIMENTS

A packaged orthodontic assembly according to one embodiment of the invention is illustrated in FIGS. 1-4 and is designated by the numeral 10. The assembly 10 broadly includes a container 12, an orthodontic appliance 14 received in the container 12, a quantity of a first orthodontic adhesive material 15 that extends across the appliance 14, a release surface 16, a quantity of a second orthodontic adhesive material 18 received on the release surface 16 and a support 20 for supporting the appliance 14 in the container 12.

In more detail, the container 12 includes an oval-shaped sidewall 22 and a bottom 24. The sidewall 22 and the bottom 24 define a chamber 26. An upper edge of the sidewall 22 is connected to a flange 28 that surrounds the chamber 26.

Figures 1, 2:
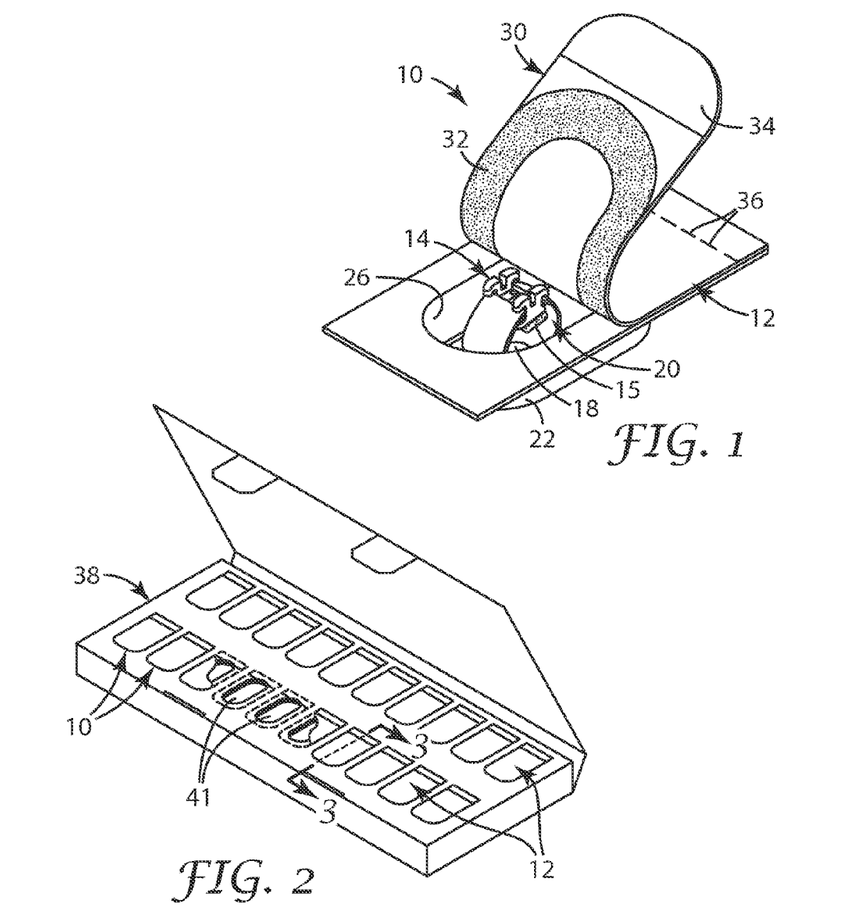
FIG. 1 is a perspective view of a packaged orthodontic assembly according to one embodiment of the present invention.
FIG. 2 is a reduced perspective view of a number of packaged orthodontic assemblies that have been received in a carrier, wherein each of the assemblies is similar to the assembly depicted in FIG. 1.
Figure 3:
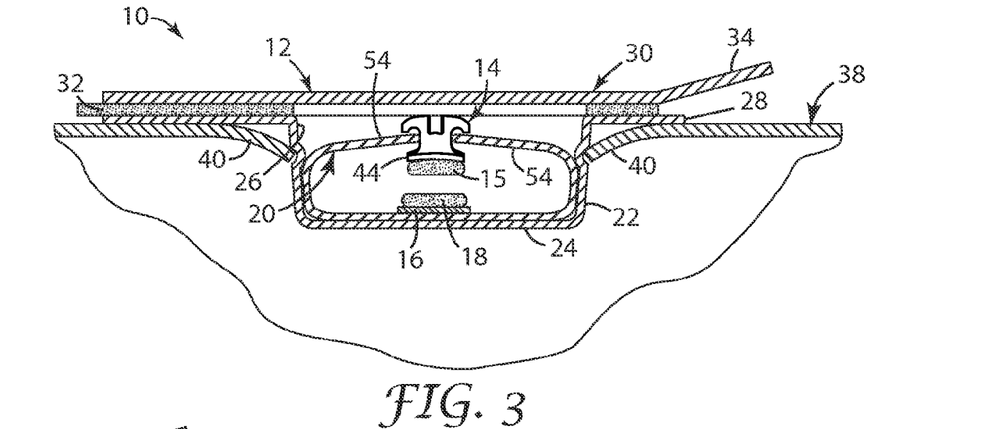
FIG. 3 is an enlarged side cross-sectional view of one of the assemblies and the carrier shown in FIG. 2, taken along lines 3-3 of FIG. 2.
Figure 4:
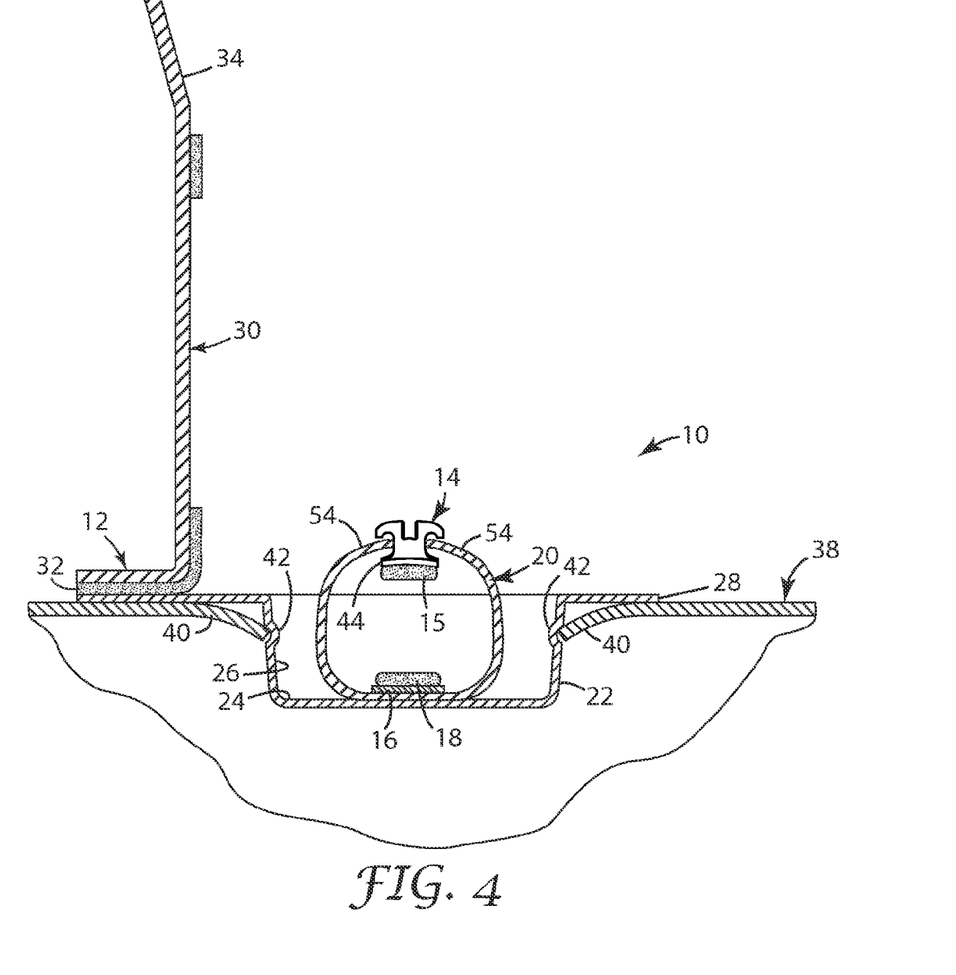
FIG. 4 is a view somewhat similar to FIG. 3 except that a cover of the assembly has been moved to an open position.

Preferably, the sidewall 22, the bottom 24 and the flange 28 are integrally molded or otherwise formed as a unitary component. Suitable materials include polyethylene terephthalate glycol ("PETG"), such as described in U.S. Pat. No. 5,328,363 (Chester et al). Optionally, a polymeric material that is compounded with metallic particles may be used, such as described in published U.S. Patent Application No. 2003/0196914 (Tzou et al).

The container 12 also includes a cover 30 that is releasably connected to the flange 28 by a section of adhesive 32. Suitable materials for the cover 30 are described in the aforementioned U.S. Pat. No. 5,328,363 (Chester et al.) and U.S. Publication No. 2003/0196914 (Tzou et al.). Suitable materials for the adhesive 32 are described in U.S. Pat. No. 5,328,363 (Chester et al.) and U.S. Pat. No. 6,960,079 (Brennan et al.). Alternatively, the cover 30 may be connected to the flange 28 by a heat seal.

The cover 30 is shown in a closed position in FIGS. 2 and 3, and is shown in an open position in FIG. 4. In its closed position, the cover 30 extends over the opening of the chamber 26 and helps protect the appliance 14 and the adhesive materials 15, 18 from exposure to light, moisture and contaminants. The cover 30 includes a tab 34 that extends past the flange 28 for gripping by the practitioner when it is desired to move the cover 30 from a closed position to an open position.

Optionally, the cover 30 includes a series of perforations 36 (FIG. 1) that facilitate self-retention of the cover 30 in its open, upright position and permit the cover 30 to be made of relatively stiff materials. The perforations 36 also provide tactile feedback to the practitioner that the cover 30 is open so that the practitioner does not continue to pull on the cover 30 and separate the cover 30 from the flange 28.

Optionally, the container 12 is received in a carrier along with other containers, such as the carrier 38 illustrated in FIG. 2. The carrier 38 has edge structure 40 (FIGS. 3 and 4) that define a series of oval-shaped openings 41 (FIG. 2). Preferably, the carrier 38 has two rows of openings 41, each row containing ten openings 41. In this manner, a space is provided to receive twenty containers similar to container 12 corresponding to each non-molar tooth involved in orthodontic treatment. Alternatively, the carrier 38 may include two rows of openings with each row containing fourteen openings 41 for those instances when appliances 14 are provided for the molar teeth as well.

The sidewall 22 of the container 12 includes two recesses 42 (FIGS. 3 and 4) that extend in a horizontal direction for receiving portions of the edge structure 40. The edge structure is flexible so that the containers 12 can be placed in or removed from the openings as desired. As shown in FIGS. 3 and 4, the edge structure 40 is slightly deformed or deflected when the container 12 is received in the opening. Normally, the deflected edge structure 40 will thereafter retain the container 12 in the opening, although sufficient urging of the container 12 will permit removal of the container 12 from the opening and detachment from the carrier 38 when desired.

Figure 5:
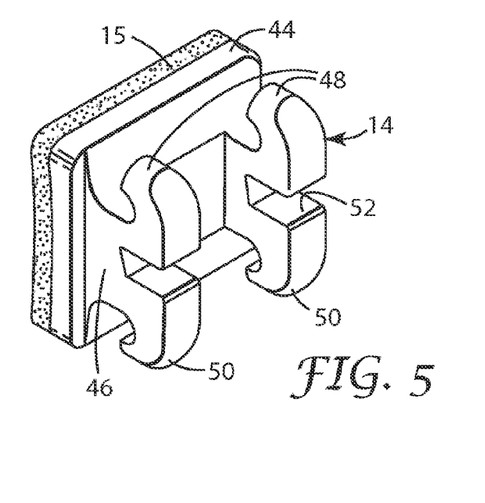
FIG. 5 is an enlarged perspective view of an orthodontic appliance of the assembly shown in FIGS. 1, 3 and 4 along with a quantity of a first adhesive material.

The appliance 14 that is illustrated in FIGS. 1, 3 and 4 is shown alone with the first adhesive material 15 in FIG. 5. In this embodiment, the appliance 14 is an orthodontic bracket, although other appliances are also possible, such as buccal tubes, buttons and other tooth attachments.

The appliance 14 includes a base 44 with a tooth-facing outer or bottom surface. The first adhesive material 15 extends across the outer surface of the base 44. A body 46 extends outwardly from the base 44 and is connected to two occlusal tiewings 48 and two gingival tiewings 50. An archwire slot 52 extends across the body 46 in the space between the tiewings 48, 50 for receiving an archwire.

Optionally, the base 44 has a custom configuration that precisely matches the shape of the patient's tooth surface. Methods of making custom bases are described in U.S. Pat. No. 5,971,754 (Sondhi et al.) and U.S. Pat. No. 7,188,421 (Cleary et al.). As one example, the custom base 44 may be formed using a hardenable adhesive material that is identical to the first adhesive material 15. Other constructions are also possible.

The appliance 14 that is illustrated in the drawings is a "twin tiewing" bracket. Other brackets are also possible, such as "single tiewing" brackets. Furthermore, the bracket may have a configuration other than that shown in the drawings. The bracket may also be made of any one of a number of materials, including metal (such as stainless steel), plastic (such as polycarbonate that is optionally filled with glass fibers) or ceramic (such as monocrystalline or polycrystalline alumina).

The support 20 is received in the chamber 12 and is releasably connected to the appliance 14. In this embodiment, the support 20 has an overall, generally "C"-shaped configuration that is attached in its central portion to the bottom 24. The support 20 includes two arms 54 that extend toward each other. Outer ends of the arms 54 are spaced apart from each other and present a channel or receptacle for receiving the appliance 14. When the appliance 14 is received in the receptacle, one of the arms 54 is located in the recesses behind the occlusal tiewings 48 (i.e., in a region between the tiewings 48 and the base 44) and the other arm 54 is located in the recesses behind the gingival tiewings 50.

The support 20 is made of a flexible material and has sufficient inherent memory to normally retain the base 44 of the appliance 14 in spaced relationship to the second adhesive material 18 as shown in FIGS. 3 and 4. Preferably, when the cover 30 of the container 12 is moved from its closed position shown in FIG. 3 to its open position as shown in FIG. 4, the inherent memory of the support 20 causes the support 20 to change its overall shape such that the arms 54 move in a direction away from the second adhesive material 18. Preferably, when the support 20 is in its relaxed configuration, the appliance 14 is outside of the chamber 26 and rests in a position above the flange 28 as depicted in FIG. 4.

Examples of suitable materials for the support 20 include flexible polymeric materials such as polyethylene, polypropylene, polyethylene terephthalate ("PET"), polyethylene terephthalate glycol ("PETG") and nylon.

The release surface 16 extends across the bottom of the support 20 near the center of its "C"-shaped configuration and faces upwardly and in a direction toward the base 44 of the appliance 14. The release surface 16 initially carries the second adhesive material 18 in a location where it faces the first adhesive material 15 and is exposed for selective contact with the first adhesive material 15 when desired as shown for example in FIG. 4. However, the release surface 16 readily releases the second adhesive material 18 when desired such that little if any of the second adhesive material 18 remains on the release surface 16. Preferably, the release surface 16 enables the second adhesive material 18 to detach without undue distortion of the overall shape of the second adhesive material 18.

The adhesive materials 15, 18 may be a liquid, a semi-liquid, a paste or a solid material that is converted into a liquid, a semi-liquid or paste during the bonding procedure. Suitable compositions include composites, compomers, glass ionomers and resin-modified glass ionomers. Examples of light-curable adhesive materials include Transbond XT brand and Transbond LR brand adhesives from 3M Unitek. Examples of chemical curing adhesive materials include Sondhi brand Rapid-Set indirect bonding adhesive, Unite brand adhesive material, and Concise brand adhesive from 3M Unitek. An example of an adhesive that is both a light-curable adhesive and a chemical curing adhesive is Multi-Cure brand glass ionomer cement from 3M Unitek.

If the adhesive materials 15, 18 are first and second components respectively of a two-component adhesive such as the chemical curing adhesive materials mentioned above, the first and second components advantageously remain out of contact with each other as illustrated in FIG. 3 during initial shipping and storage of the container 12. Optionally, if one of the components comprises lyophilic ionic cement, the cement may be fixed to the base 44 by the methods described in U.S. Pat. No. 6,050,815 (Adam et al.).

Compositions useful for the adhesive materials 15, 18 of the present invention are well known to one of skill in the art. Useful compositions include, for example, both light cure and chemical cure orthodontic adhesives. In some embodiments, the compositions are preferably fluoride releasing adhesives, self-etching adhesives, self-priming adhesives, color-changing adhesives, and combinations thereof.

Optionally, each of the adhesive materials 15, 18 falls in one of the following classes in accordance with the practitioner's preferences for tooth treatment:

Class I: An adhesive that requires both etching of tooth enamel and a separate application of a primer to the tooth enamel.

Class II: An adhesive that requires etching but not necessarily a separate application of primer.

Class III: An adhesive that requires no treatment of the teeth other than cleaning.

Class I adhesives, which include some chemically cured adhesives, require the use of a suitable etchant such as phosphoric acid or bisphosphonic acid. Possible primers for use with class I adhesives include orthodontic primers such as Transbond MIP brand primer and Transbond XT brand primer from 3M Unitek and Ortho Solo brand primer from Ormco Corporation. A self-etching primer may possibly be used, such as Transbond Plus SEP brand primer from 3M Unitek. Optionally, the primer may include a photobleachable dye to ensure adequate coverage of the primer on the teeth, a small amount of fluoroalumina silicate glass ("FAS" glass) for providing fluoride release during treatment, a small amount of fumed silica for rheology control purposes, and/or a small amount of silanated quartz filler for enhanced fracture toughness.

Suitable class II adhesives, which include many conventionally light cured adhesives, do not require a separate priming step. If the adhesive is a multi-layer adhesive, the adhesive may include a layer of primer that first contacts the tooth during a bonding procedure. As mentioned previously, phosphoric acid or bisphosphonic acid may be used as an etchant. If the adhesive does not include a primer component, the etchant itself may function as a primer. An example of such a self-etching primer is Transbond Plus SEP brand primer from 3M Unitek. Optionally, the self-etching primer could incorporate the optional features described above for the class I adhesive.

Suitable class III adhesives avoid the need for etching and priming the teeth and may be referred to as "self-adhesive" compositions. With these adhesives, the practitioner need only clean the teeth prior to application of the dental appliance in a typical bonding procedure. Suitable class III adhesives may include an acid component selected from a methacrylate phosphate (e.g., mono-HEMA phosphate, di-HEMA phosphate, glycerol dimethacrylate (GDMA) phosphate, a solution of a bisphosphonic acid in water or other solvent, and a bisphosphonic acid in powder form (using water for ionizing that is left on the teeth after tooth prophy and rinse). Other class III adhesives may include an ethylenically unsaturated component with acid functionality, an ethylenically unsaturated component without acid functionality, an initiator system, and a filler. Optionally a class III adhesive may be essentially free of water. Examples of class III adhesives have been previously described, e.g. in published U.S. Patent Application Nos. 2005/0176844 (Aasen et al.), 2005/0175966 (Falsafi et al.) and 2005/0175965 (Craig et al.).

The class III adhesives described above can optionally incorporate fillers (e.g., a glass ionomer-type filler that binds the water in the usual glass ionomer setting reaction). In addition, any of the class III adhesives described above may incorporate the optional features described in connection with class I adhesives.

Adhesive materials useful in the present invention may optionally include components such as fluoride releasing agents as described, for example, in U.S. Pat. No. 3,814,717 (Wilson et al.) and U.S. Pat. No. 6,126,922 (Rozzi et al.); adhesive enhancing agents (e.g., titanates, zirconates) as disclosed, for example, in PCT International Publication No. WO 00/69393 (Brennan et al.); fillers; micro fillers; remineralisation agents; enzyme releasing agents; rheology enhancing agents; photobleachable dyes; thermochromic agents; and combinations thereof.

Optionally, one or both of the adhesive materials 15, 18 preferably have an initial color remarkably different than dental structures. Color is preferably imparted to the adhesive materials 15, 18 through the use of a photobleachable dye. The adhesive materials 15, 18 preferably include at least 0.001% by weight photobleachable dye, and more preferably at least 0.002% by weight photobleachable dye, based on the total weight of the adhesive material. The adhesive materials 15, 18 preferably include at most 1% by weight photobleachable dye, and more preferably at most 0.1% by weight photobleachable dye, based on the total weight of the adhesive material. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, ambient moisture, and the type and weight percent of filler and/or resin. However, the bleaching properties of the dye can be readily determined by irradiating the adhesive material and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof. Reactant dyes may also be used.

The color change in the adhesive materials 15, 18 is preferably initiated by light. Preferably, the color change is initiated using actinic radiation using, for example, a dental curing light which emits visible or near infrared (IR) light for a sufficient amount of time. The mechanism that initiates the color change in the adhesive materials 15, 18 may be separate from or substantially simultaneous with the hardening mechanism that hardens the resin. For example, the adhesive materials 15, 18 may harden when polymerization is initiated chemically (e.g., redox initiation) or thermally, and the color change from an initial color to a final color may occur subsequent to the hardening process upon exposure to actinic radiation.

The change in adhesive material color from an initial color to a final color is preferably quantified by a Color Test as described below. Using the Color Test, a value of $\Delta E^*$ is determined, which indicates the total color change in a 3-dimensional color space. The human eye can detect a color change of approximately 3 $\Delta E^*$ units in normal lighting conditions. The dental adhesive material of the present invention is preferably capable of having a color change, $\Delta E^*$, of at least 10; more preferably, $\Delta E^*$ is at least 15; most preferably $\Delta E^*$ is at least 20.

In one embodiment of the invention, the adhesive materials 15, 18 are identical in composition and properties. The first adhesive material 15 is present in an amount determined in advance by the manufacturer to be sufficient for bonding the appliance 14 to a patient's tooth with relatively little excess first adhesive material 15. As such, when the appliance 14 is pressed against the tooth surface by the practitioner during a bonding procedure, relatively little adhesive flash is expelled along the sides of the appliance base 44. Consequently, the time for removing such adhesive flash is reduced.

However, if the practitioner desires to bond the appliance 14 to the patient's tooth with a quantity of adhesive that is greater than the quantity of the first adhesive material 15, the practitioner may elect to push the appliance 14 while within the container 12 in a downward direction and away from the practitioner in order to add at least a portion of the second adhesive material 18 to the first adhesive material 15. The practitioner's decision to use the second adhesive material 18 may be due, for example, to the practitioner's preference for ensuring that no gaps or voids are present between the appliance 14 and the patient's tooth which might otherwise unduly weaken the bond strength of the appliance 14 and/or present a cavity where food may tend to collect. As another example, the practitioner may elect to use the second adhesive material 18 in instances where the surface of the patient's tooth has an irregular shape or where a buildup of adhesive is desired to support the appliance 14 in a certain orientation.

In another embodiment of the invention, the first adhesive material 15 differs in composition and/or properties from the composition and properties of the second adhesive material 18. For example, the second adhesive material 18 may comprise a primer to provide a lower viscosity wetting agent. Optionally, the primer is a self-etching primer that provides a wetting agent as well as reactive self-etching moieties. In another embodiment, the second adhesive material 18 is a primer that includes an amount of photobleachable dyes, such as the dyes mentioned above.

Optionally, the second adhesive material 18 is a liquid composition that enhances the properties of the first adhesive material 15. For example, the second adhesive material 18 when transferred to the first adhesive material 15 may increase the tackiness of the first adhesive material 15, may increase the wettability of the first adhesive material 15 and/or may enhance the moisture tolerant characteristics of the first adhesive material 15. These enhanced properties may facilitate bonding of the appliance 14 and also decrease the likelihood of spontaneous debonding of the appliance 14 during the course of orthodontic treatment.

Particularly preferred liquid compositions that comprise the second adhesive material 18 include hydrophilic compositions that are compatible with the first adhesive material 15, such as some of the liquid orthodontic primers that are commercially available. An example of a suitable primer is Transbond MIP brand primer from 3M Unitek. The liquid composition may include one or more monomers, oligomers, polymers or copolymers or mixtures of the foregoing. The liquid composition may also contain additives such as pigments, antioxidants and/or curatives (to enhance curing properties of the adhesive material 18). The liquid composition optionally contains solid filler particles such as fumed or fused silica, fluoroaluminosilicate, quartz, zirconia, and the filler particles could optionally be coated for example with silane, zirconate or titanate coatings as dispersion aids. The liquid composition may also include a fluoride releasing material such as zinc fluoride. Other possible remineralisation agents include amorphous calcium phosphate, casein phosphopeptides and complexes of the same. As another option, the liquid composition may include antimicrobial agents and/or a material that serves to etch the tooth enamel when placed into contact with a tooth.

Preferably, the liquid composition includes hydrophilic monomers, oligomers, polymers or blends thereof that optionally have the ability to absorb moisture and also provide enhanced chemical bonding to tooth enamel. Preferably, curing is conducted at the interface of the liquid composition and the first adhesive material 15 such that strong bonds are formed. Preferably, the liquid composition "cures to" the first adhesive material 15 as the adhesive hardens, i.e., the liquid composition polymerizes with the first adhesive material 15. The liquid composition is wholly or partially crosslinked to the first adhesive material 15 as the first adhesive material 15 hardens. Furthermore, the liquid composition is preferably substantially immiscible with the first adhesive material 15 over an extended period of time, so that the liquid composition does not unduly mix with or dissolve into the adhesive before the adhesive cures.

Preferred moisture tolerant or hydrophilic materials for the liquid composition include 2-hydroxyethyl acrylate, 2-hydroxyethyl methacrylate ("HEMA"), hydroxypropyl acrylate, hydroxypropyl methacrylate, glycerol di-acrylate, glycerol di-methacrylate, polyethylene glycol mono methacrylate, polypropylene glycol mono methacrylate, tetrahydrofurfuryl acrylate, tetrahydrofurfuryl methacrylate, glycidyl acrylate, glycidyl methacrylate and the like. Other preferred hydrophilic monomers include glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30, especially triethylene glycol dimethacrylate ("TEGDMA")).

More specific examples of hydrophilic materials are non-ionic polymers or copolymers, e.g. polyalkylene oxides (polyoxymethylene, polyethyleneoxide, polypropylene oxide), polyethers (polyvinylmethyl ether), polyethyleneimine copolymers, polyacrylamides and polymethacrylamides, polyvinylalcohol, saponified polyvinylacetate, polyvinylpyrrolidone, polyvinyloxazolidone, and polymers containing N-oxysuccinimido groups. Other examples of hydrophilic materials include ionic or ionizable polymers and copolymers containing polyacrylic acid, polymethacrylic acid in unionized, partially neutralized or fully neutralized form, polyethyleneimine and its salts, polyethylene sulfonic acid and polyaryl sulfonic acids in unionized, partially neutralized or fully neutralized form, polyphosphoric and polyphosphonic acids in unionized, partially neutralized or fully neutralized form.

Preferred hydrophilic materials may be prepared by reaction of vinylic monomers such as acrylates, methacrylates, crotonates, itaconates and the like that contain polar groups that are acidic, basic or provided as a salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quarternary ammonium, carboxylate salt, sulfonic acid salt and the like) and the precursors and protected forms of these groups.

Other possible liquid compositions for the second adhesive material 18 include hydrophobic materials. Examples of suitable hydrophobic materials include Bisphenol A diglycidyl ether dimethacrylate (bisGMA), Ethoxylated$_2$ Bisphenol A Dimethacrylate (bisEMA6), Ethoxylated$_6$ Bisphenol A Dimethacrylate (Diacryl 101 or bisEMA2).

Particularly preferred materials for the release surface 16 include polymeric foams having either an open cellular structure or a closed cellular structure. A closed cell foam is preferred. The release surface 16 is preferably compressible and preferably resilient.

Preferably, the upper side of the release surface 16 has pores with a diameter that are mostly, if not entirely, within the range of about 0.00005 inch (0.001 mm) to about 0.03 inch (0.8 mm). More preferably, the diameter of the pores is mostly, if not entirely, within the range of about 0.001 inch (0.02 mm) to about 0.01 inch (0.2 mm). An example of a suitable average pore size is 0.004 inch (0.1 mm) in diameter or alternatively in the range of about 0.006 inch (0.15 mm) to about 0.01 inch (0.2 mm). The pore size is determined by determining its diameter in a reference plane parallel to the plane of the upper face. If the pore does not present a circular shape in that reference plane, the pore size is determined by calculating the diameter of a circle presenting an area that is equal to the area of the pore in such reference plane.

Particularly preferred foam materials for the release surface 16 include polyolefin foams such as polyethylene foams, polybutylene foams and polypropylene foams, or blends of the foregoing. Polyvinyl chloride foams, polyurethane foams and foam copolymers may also be employed. Examples of suitable polyethylene foams include L series, M series, S series and T series Minicel brand foams (such as series M200, M300 and T300) from Voltek. Another suitable foam is Volara brand 9EO skived foam from Voltek. Optionally, an outer layer of cells of the foam may be heated to "seal" or shrink the size of the pores by reducing the pore diameter and/or by reducing the pore depth in directions perpendicular to the plane of the upper face.

If the selected foam is shown to absorb one or more of the fluid components of the second adhesive material 18 over time, then the foam could be modified in some manner provided the release characteristics of the foam are not unduly impaired. For example, the upper face of the release surface 16 could be fused or coated with an organic or inorganic barrier material to partially close some or all of the pores. Optionally, the barrier material is a curable monomeric system that is cured or partially cured to establish a crosslinked barrier, either at the upper face, in the body of the foam material, or both. As another option, the foam is coated or partially coated (and possibly immersed) in a liquid component that reduces the driving force for further absorption.

The release surface 16 may alternatively be made of other materials as well. For example, the release surface 16 may be made of other polymers, copolymers or blends of polymers and copolymers such as polyesters, polyolefins, polyurethanes, fluoropolymers, (meth)acrylic, silicones, epoxies, synthetic rubbers, polycarbonates or vinyls. The release surface 16 may also be made of ceramic, glass or metal. Optionally, the inner surface of the support 20 facing the adhesive material 15 presents the release surface 16 so that the application of a separate coating or layer to the support 20 is unnecessary; in these instances, low surface energy coatings such as silicones or fluoropolymers may be applied to the support 20 to facilitate release of the second adhesive material 18.

When the release surface 16 is made of a material other than a foam as described above, the optional pores in the preferred embodiments mentioned above may be made using any other suitable process or structure. For example, a number of particles such as spherical or irregularly-shaped beads, shards or particles made of glass, ceramic, metal or other materials may be fixed to a backing layer of the release surface 16 to provide pores. As another alternative, the upper face may have ridges, projections or other structure, either random or repeating, to provide a number of small pores. The pores may be made using a micro-replication technique, such as the methods disclosed in U.S. Pat. No. 5,152,917 (Pieper et al.) and U.S. Pat. No. 5,500,273 (Holmes et al).

Optionally, the release surface 16 includes a quantity of a liquid composition that extends across the upper face and is in contact with the second adhesive material 18. The liquid composition may be either a contiguous layer of liquid or a non-contiguous layer, such a patterned or printed coating or a coating randomly applied. The liquid composition may be made of any liquid material that facilitates release of the second adhesive material 18 from the release surface 16 when desired, and if curable may be uncured, partially cured or entirely cured when present in the assembly 10.

Preferably, the liquid composition is at least partially removed from the release substrate when the second adhesive material 18 detaches from the release surface 16, and remains with the second adhesive material 18 during bonding of the appliance 14 to the patient's tooth.

Additional information regarding the release surface 16, including other alternative constructions and materials, may be found in U.S. Pat. No. 6,183,249 (Brennan et al.). Additional information regarding suitable hydrophilic materials may be found in U.S. patent application Ser. No. 09/311,606, filed May 13, 1999 (Brennan et al.). Optionally, the release surface 16 may comprise part of the support 20, or be a coating that is applied to the support 20.

A useful method for applying the second adhesive material 18 to the release surface 16 includes, for example, using automated fluid dispensing systems such as those available under the trade designation Automove from Asymtek (Carlsbad, Calif.). Such automated fluid dispensing systems are useful for dispensing both patterned and non-patterned coatings and layers. Inkjet dispensing systems such as inkjet printers are also useful for applying patterned and non-patterned liquid coatings and layers. Other useful systems include, for example, piston dispensing systems and multiple resolution fluid applicators as described, for example, in U.S. Pat. No. 6,513,897 (Tokie). Examples of appliances 14 that are precoated by the manufacturer with an adhesive (such as first adhesive material 15) include APC brand adhesive precoated appliances, from 3M Unitek Corporation.

An example of use of the assembly 10 will now be described. When the practitioner desires to use the appliance 14 in treatment, the container 12 is opened by moving the cover 30 from its closed position as shown in FIG. 3 to its open position as shown in FIG. 4. As the cover 30 is opened, the inherent resiliency of the support 20 causes the configuration of the support 20 to move to its normal, relaxed shape as shown in FIG. 4. In this configuration of the support 20, the arms 54 as well as the appliance 14 and the first adhesive material 15 have been moved upward and away from the second adhesive material 18 and to positions away from their respective positions when the cover 30 is closed.

Preferably, the appliance 14 is moved by the support 20 to a position above the flange 28 once the cover 30 has been opened. As such, grasping of the appliance 14 with a hand instrument such as a bracket placement tool or tweezers is facilitated. As one example, the practitioner may grasp opposite sides of the appliance 14 with jaws of the tweezers for subsequent handling.

Next, and in those instances when the practitioner elects to add the second adhesive material 18 to the first adhesive material 15, the practitioner pushes the appliance 14 in a downward direction until the first adhesive material 15 contacts the second adhesive material 18. The support 20 including the arms 54 is sufficiently flexible to enable the appliance 14 to be moved toward the release surface 16 without undue effort. Once the first adhesive material 15 has been pressed against the second adhesive material 18, pressure on the appliance 14 by the practitioner is relieved and the appliance 14 is moved in an upward direction. As the appliance 14 moves in a direction away from the bottom 24 of the container 12, the second adhesive material 18 detaches from the release surface 16 and remains coupled to the first adhesive material 15.

After the appliance 14 has been moved above the flange 28, the appliance 14 is shifted in a lateral direction (i.e., in a mesial or distal direction, or in a direction along the longitudinal axis of the archwire slot 52). As the appliance 14 is so moved, the tiewings 48, 50 move along the space between the arms 54 until such time as the appliance 14 is clear of the support 20. Optionally, the hand instrument used to grasp the appliance 14 may be maneuvered in such a manner to tilt the appliance 14 while the appliance 14 is still in contact with the arms 54 and then move the appliance 14 along the arms 54 in the direction of the upward tilt. The appliance 14 may then be placed directly on the patient's tooth by the practitioner as desired.

Figure 6:
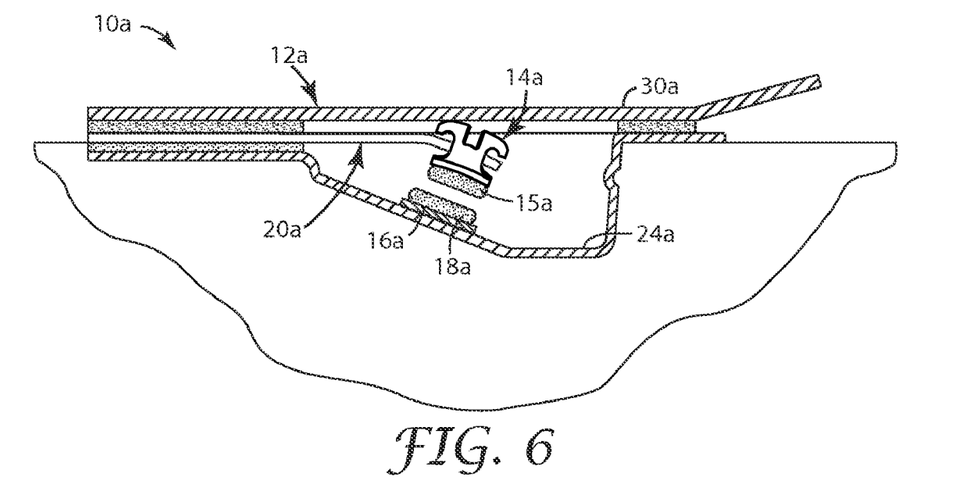
FIG. 6 is a view somewhat similar to FIG. 3 but showing a packaged orthodontic assembly constructed in accordance with another embodiment of the invention.

A packaged orthodontic assembly 10a according to another embodiment of the invention is illustrated in FIG. 6. The assembly 10a includes a container 12a, an appliance 14a, a first adhesive material 15a, a release surface 16a, a second adhesive material 18a and an elongated support 20a. Except as described below, the assembly 10a is substantially similar to the assembly 10 and consequently a description of the common aspects need not be repeated.

Figure 7:
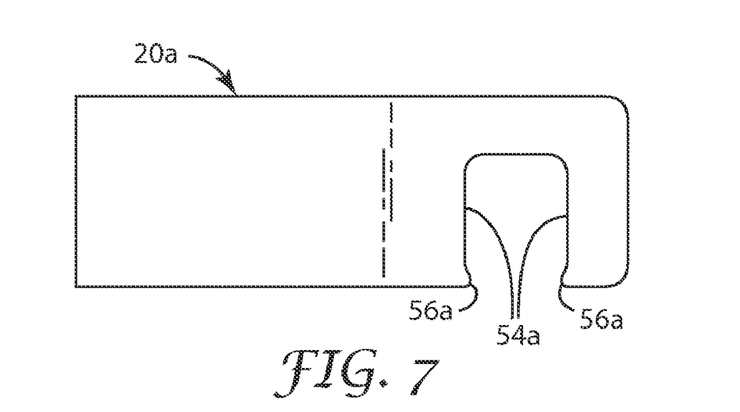
FIG. 7 is a plan view of a support alone of the assembly illustrated in FIG. 6.

The support 20a has a generally flat planar configuration when the container 12a is closed as shown in FIG. 6. A top view of the support 20a alone is illustrated in FIG. 7. An outer, free end of the support 20a includes two edges or arms 54a that are spaced apart from each other to present an opening. Optionally, one or both of the arms 54a includes a small protrusion 56a to help releasably retain the appliance 14a in the opening or space between the arms 54a.

The support 20a is resilient and has inherent memory. During opening of the container 12a, the support 20a relaxes and moves its outer, free end in an upward direction in a swinging, pivotal manner, causing the arms 54a to move the appliance 14a along with the first adhesive material 15a in a direction away from a bottom 24a of the container 12a. Once the container 12a has been opened and the support 20a has relaxed, the support 20a preferably has a configuration such that the arms 54a are spaced above the flange of the container 12a.

Optionally, the bottom 24a of the container 12a extends in an inclined direction relative to the flange of the container 12a and to the longitudinal axis of the support 20a, and the release surface 16a extends across the bottom 24a in facing but in spaced-apart relationship to the first adhesive material 15a when the container 12a is closed. Once a cover 30a of the container 12a has been opened, the sides of the appliance 14a may be grasped with a tweezers or other hand instrument as described above in connection with the appliance 14.

If the practitioner elects to add the second adhesive material 18a to the first adhesive material 15a, the practitioner pushes the appliance 14a in a downward direction along with the support 20a until such time as the first adhesive material 15a contacts the second adhesive material 18a. The second adhesive material 18a then transfers to the first adhesive material 15a. Next, pressure is relieved on the appliance 14a and the latter is allowed to move in an upward direction in a swinging manner.

Once the appliance 14a and the arms 54a of the support 20a have been moved to a position above the flange of the container 12a, the appliance 14a may be detached from the support 20a by moving the appliance 14a along the arms 54a. The appliance 14a, once clear of the support 20a, is then available for placement by the practitioner on the surface of a patient's tooth.

Figure 8:
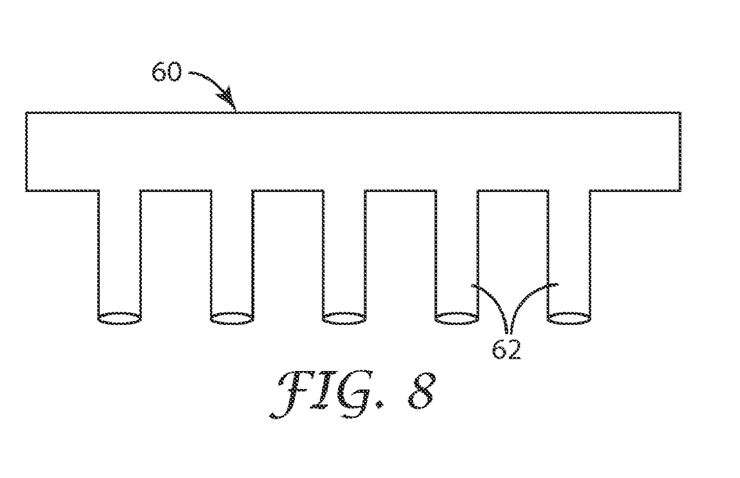
FIG. 8 is a side elevational view of a tool for use with the assembly as shown in FIGS. 1-7.

FIG. 8 is a side view of a tool 60 that may be used with the present invention, including the assemblies 10, 10a described above. The tool 60 includes a row of elongated fingers 62 arranged in spaced-apart relation. As one example, and as shown in the drawings, five fingers 62 are provided. However, the tool 60 may have a smaller or greater number of fingers as an alternative.

The spacing between the fingers 62 is approximately equal to the spacing between the containers 12 when received on the carrier 38 shown in FIG. 2. Once the covers 30 of the containers 12 have been opened, the tool 60 may be used by the practitioner to apply adhesive material 18, 18a to the adhesive material 15, 15a on the base of each appliance 14, 14a simultaneously. The fingers 62 bear against each appliance 14, 14a simultaneously to move each appliance 14, 14a in a downward direction and toward the adjacent, corresponding quantity of the second adhesive material 18, 18a. The tool 60 may then be lifted to disengage the fingers 62 from the appliances 14, 14a at once, whereupon the appliances 14, 14a may be individually grasped and placed on the patient's teeth as desired.

Optionally, the length of the finger 62 is selected to correspond with the distance between the facial surface of the appliance 14, 14a and the top flange of the container 12, 12a when the first adhesive material 15, 15a is in firm contact with the second adhesive material 18, 18a. Such construction helps the user to avoid pushing the appliance 14, 14a too far into the chamber (such as chamber 26) and unduly distorting the shape of either the first adhesive material 15, 15a or the second adhesive material 18, 18a.

Figure 9:
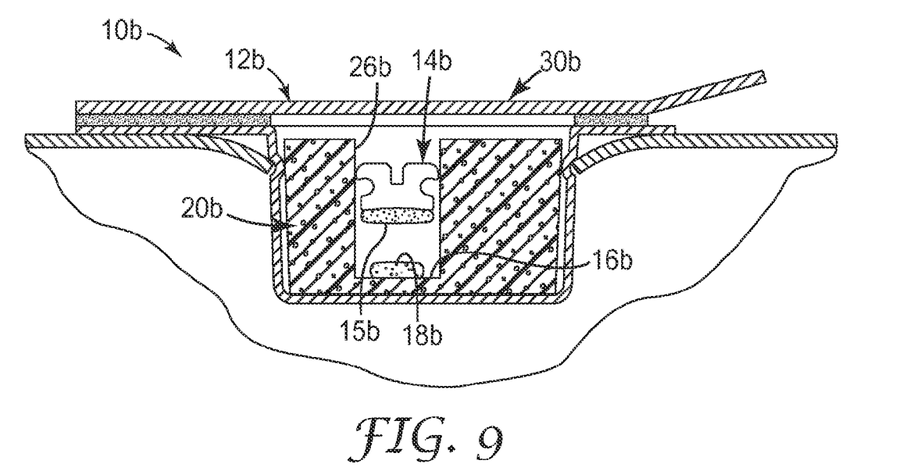
FIG. 9 is a side cross-sectional view of a packaged orthodontic assembly according to a further embodiment of the invention.

A packaged orthodontic assembly 10b according to another embodiment of the invention is illustrated in FIG. 9. The assembly 10b includes a container 12b, an appliance 14b, a first adhesive material 15b, a release surface 16b, a second adhesive material 18b and a support 20b. As in the embodiments described above, the first adhesive material 15a is preferably applied to a base of the appliance 14b by the manufacturer. A cover 30b, similar to covers 30, 30a extends over an opening of a chamber 26b and is shown in a closed position in FIG. 9.

In this embodiment, the support 20b comprises a section of compressible foam material having a cavity for releasably receiving the appliance 14b. At the bottom of the cavity, a central upwardly facing surface of the support 20b comprises the release surface 16b. The inner dimensions of the cavity are selected to enable the foam member to bear against and support the appliance 14b in a suspended relationship, such that the first adhesive material 15b is normally spaced from the second adhesive material 18b. As one option, the cavity in the foam member includes vertically-extending recesses that extend along mesial and distal sides of the appliance 14b so that a hand instrument such as a pair of tweezers can be more readily maneuvered into a position to grasp the mesial and distal sides of the appliance 14b. As another option, the support 20b is reduced in height from the height shown in FIG. 9, and the facial surface of the appliance 14b is initially located above the top of the support 20b (similar to the orientation of the appliance 14c in FIG. 10) to facilitate grasping of the appliance 14b.

As one option, the appliance 14b may be lifted from the cavity of the support 20b and out of the chamber 26b in instances where use of the second adhesive material 18b is not desired. However, if the use of the second adhesive material 18b is desired, the practitioner moves the appliance 14b in a downward direction until the first adhesive material 15b contacts the second adhesive material 18b. Once contact is established, the appliance 14b, together with the first adhesive material 15b and at least a portion of the second adhesive material 18b is lifted from the cavity and out of the chamber 26b. Preferably, the inner walls of the support 20b facing the cavity are constructed to bear against the appliance 14b with sufficient force to support the appliance 14b in a stable, suspended relationship during shipping and handling of the assembly 10b, but enable the appliance 14b to be lifted and released from the support 20b without undue effort.

Other aspects of the orthodontic assembly 10b are similar to aspects of the assemblies 10, 10a described above.

Figure 10:
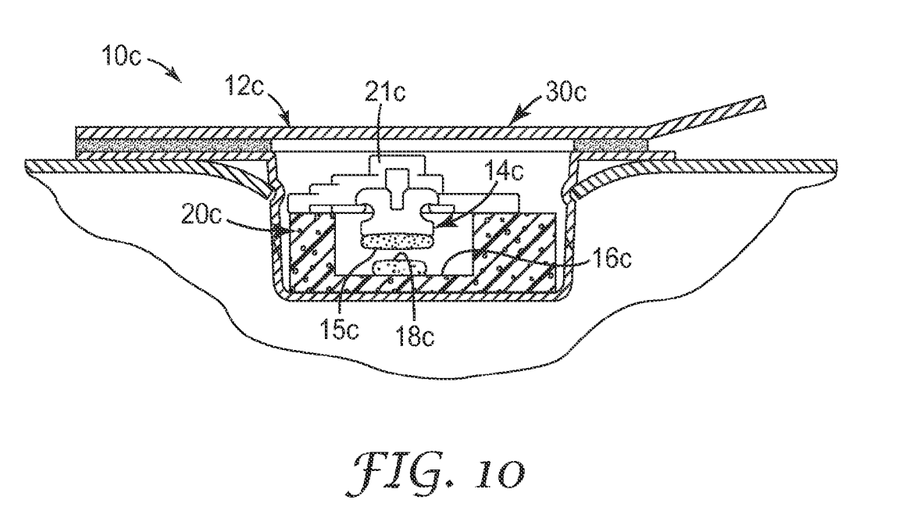
FIG. 10 is a side cross-sectional view of a packaged orthodontic assembly constructed in accordance with yet another embodiment of the invention.

A packaged orthodontic assembly 10c according to another embodiment of the invention is illustrated in FIG. 10. The assembly 10c includes a container 12c, an appliance 14c, a first adhesive material 15c, a release surface 16c, a second adhesive material 18c and a support 20c. In addition, the assembly 10c includes a positioning member 21c that is removably received in a "vertical" channel of the appliance 14c (i.e., a channel extending between spaced apart tiewings of the appliance 14c in an occlusal-gingival direction, considered when viewing the appliance 14c after the appliance 14c is bonded to the patient's tooth). Examples of suitable positioning members 21c include long axis indicators that are provided to help the practitioner align the appliance 14c with the longitudinal axis of the tooth during a bonding procedure.

As shown in FIG. 10, the support 20c includes a central cavity with an upwardly facing surface that comprises the release surface 16c. The top of the support 20c includes a pair of grooves (not shown) that releasably receive bottom edges of the positioning member 21c when the container 12c is closed as illustrated in FIG. 10. Preferably, the positioning member 21c is sandwiched between the top surface of the support 20c and the bottom surface of a cover 30c when the container 12c is closed in order to prevent undue jostling or other movement of the appliance 14c during shipping and handling of the assembly 10c. Preferably, the positioning member 21c includes shoulders (as shown) or other indicating marks or structure to help the practitioner place the appliance 14c in a precise position a predetermined distance away from the occlusal tip of the patient's tooth during a bonding procedure.

In instances where the practitioner elects to not use the second adhesive material 18c in the bonding procedure, the appliance 14c can be removed from the container 12c as soon as the cover 30c is opened. To this end, the sides of the appliance 14c may be grasped by a hand instrument such as tweezers. As another option, the practitioner may elect to grasp the sides of the positioning member 21c for manipulating the appliance 14c.

Alternatively, if the practitioner elects to add some or all of the second adhesive material 18c to the first adhesive material 15c, the appliance 14c is moved in a downward direction viewing FIG. 10 by pushing on the appliance 14c or the positioning member 21c such that the bottom edges of the long axis indicator 21c compress the support 20c. Continued movement of the appliance 14c in a downward direction brings the first adhesive material 15c into contact with the second adhesive material 18c. The appliance 14c can then be lifted out of the container 12c for bonding to the patient's tooth. Other aspects of the orthodontic assembly 10c are similar to corresponding aspects of the assemblies 10, 10a and 10b described above.

Figure 11:
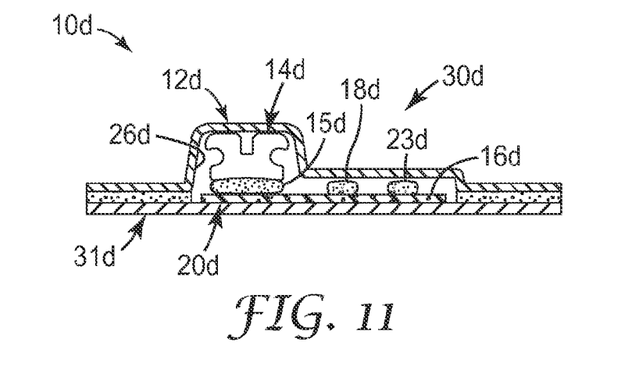
FIG. 11 is a side cross-sectional view of a packaged orthodontic assembly that is constructed in accordance with still another embodiment of the invention.

A packaged orthodontic assembly 10d according to a further embodiment of the invention is illustrated in FIG. 11. The assembly 10d includes a container 12d, an orthodontic appliance 14d, a first adhesive material 15d extending across a base of the appliance 14d, a release surface 16d, a second adhesive material 18d and a support 20d. The assembly 10d also includes a third adhesive material 23d that is spaced from the first adhesive material 15d and the second adhesive material 18d within a chamber 26d of the container 12d.

In the embodiment depicted in FIG. 11, the container 12d includes a dome-shaped cover 30d having a lower peripheral flange that is releasably secured to an outer edge of the support 20d. The release surface 16d is contained within the chamber 26d when the container 12d is closed. However, as an alternative, the area of the release surface 16d may be co-extensive with the area of the upper surface of the support 20d, such that the flange of the cover 30d is releasably secured to an outer edge of the release surface 16d instead of an outer edge of the support 20d. Preferably, the shape of the cover 30d is selected to avoid excessive free space within the chamber 26d. Although not shown in the drawings, the container 12d may also include sections of light-blocking films, such as a section of light-blocking film that covers either side of the support 20d.

The first adhesive material 15d is pre-applied to the base of the appliance 14d by the manufacturer and is in contact with the release surface 16d. The second adhesive material 18d and the third adhesive material 23d are applied directly to the release surface 16d. Both of the adhesive materials 18d, 23d are initially spaced apart from the appliance 14d and the first adhesive material 15d when the container 12d is closed. Once the cover 30d is opened, the practitioner may elect to bond the appliance 14d to the patient's tooth using only the first adhesive material 15d, or may instead elect to add either or both of the adhesive materials 18d, 23d to the adhesive material 15d before bonding the appliance 14d to the patient's tooth.

As one example, the practitioner may grasp the mesial and distal sides of the appliance 14d after the container 12d is opened and move the appliance 14d toward the second adhesive material 18d in order to scoop up all or a potion of the second adhesive material 18d. If use of the third adhesive material 23d is also desired, the practitioner may continue movement of the appliance 14d toward the third adhesive material 23d until all or a portion of the latter is also wiped up and added to the adhesive materials 15d, 18d. In this example, each of the adhesive materials 18d, 23d may be present in a known quantity equal to 20% of the weight of the first adhesive material 15d. As a result, the practitioner can elect to increase, if desired, the total weight of adhesive material on the appliance 14d by approximately 20% by scooping up the adhesive material 18d, or by approximately 40% by scooping up both the second adhesive material 18d and the third adhesive material 23d.

As other alternatives, the assembly 10d may include only a single extra known quantity of adhesive material (such as adhesive material 18d), or three or more extra known quantities of adhesive material (similar, for example, to adhesive materials 18d and 23d). Other aspects of the assembly 10d are similar to corresponding aspects of the assemblies 10, 10a, 10b and 10c described above.

Figure 12:
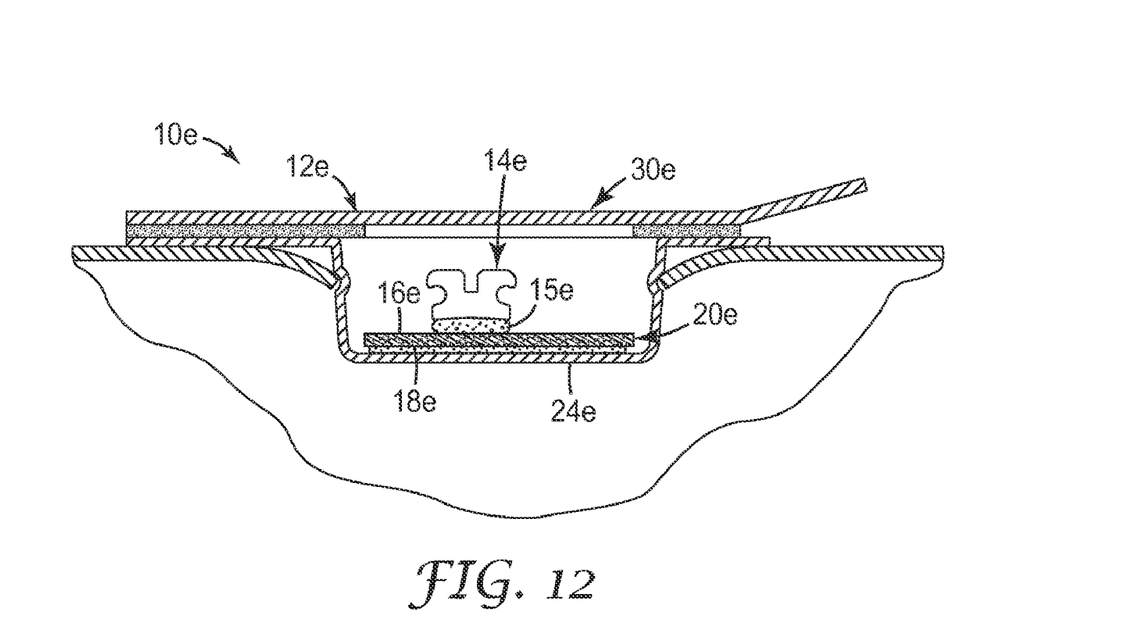
FIG. 12 is a side cross-sectional view of a packaged orthodontic assembly that is constructed in accordance with still another embodiment of the invention.

A packaged orthodontic assembly 10e according to still another embodiment of the invention is illustrated in FIG. 12. The assembly 10e includes a container 12e, an appliance 14e, and a first adhesive material 15e extending across the base of the appliance 14e. The first adhesive material 15e is in contact with a release surface 16e that, in this embodiment, is the upper surface of a support 20e. A second adhesive material 18e extends in a layer between the bottom of the support 20e and the upper surface of a bottom 24e of the container 12e. A cover 30e is movable from a closed position to an open position in order to gain access to the appliance 14e when desired.

In the embodiment depicted in FIG. 12, the practitioner may elect to bond the appliance 14e to the patient's tooth using the first adhesive material 15e. However, in instances where use of the second adhesive material 18e is also desired, the support 20e may be removed from the container 12e after the appliance 14e has been lifted away from the release surface 16e. The second adhesive material 18e can then be added to the first adhesive material 15e, either by manipulating the appliance 14e to bring the first adhesive material 15e into contact with the second adhesive material 18e or by using a hand instrument (such as a spatula) to scoop up all or a portion of the second adhesive material 18e and apply the same to the first adhesive material 15e.

Figure 13:
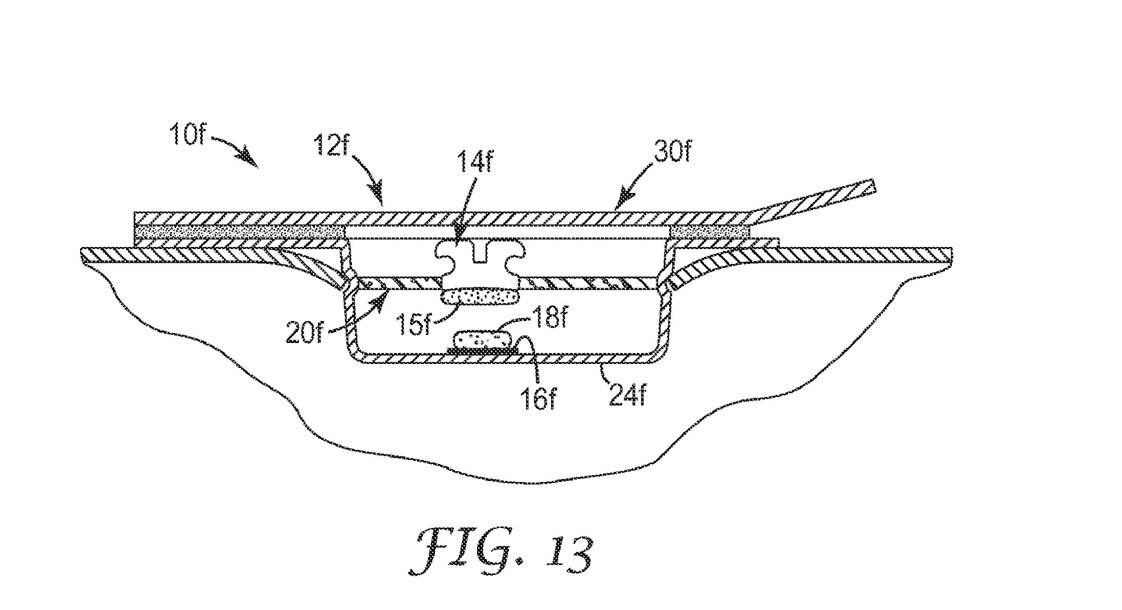
FIG. 13 is a side cross-sectional view of a packaged orthodontic assembly that is constructed in accordance with an additional embodiment of the invention.

A packaged orthodontic assembly 10f that is constructed in accordance with yet another embodiment of the invention is depicted in FIG. 13. The assembly 10f includes a container 12f with a cover 30f, an appliance 14f, and a first adhesive material 15f extending across the base of the appliance 14f. A second adhesive material 18f sits atop a section of release surface 16f that is affixed to a bottom 24f of the chamber within the container 12f. Alternatively, the bottom 24f of the chamber could be coated or otherwise manufactured to provide a suitable release surface for the second adhesive material 18*f*.

A support 20*f* is made of a material that is compatible with the first adhesive material 15*f*. Optionally, the support 20*f* comprises a flexible, rigid or semi-rigid foam material. The support 20*f* may also comprise an elastomeric material. In the illustrated embodiment, the support 20*f* is sized to be in compression against the inner walls of the chamber such that the resulting force fit relationship serves to hold the support 20*f* in place in the container 12*f*. Alternatively, or in addition to, the container 12*f* could be provided with an inner ledge, shelf, notch or other structure that receives the perimeter of the support 20*f*.

The appliance 14*f* is received in a slit or opening of the support 20*f*. Once the container 12*f* is opened, the practitioner can grasp the appliance 14*f* by its sides, such as its mesial and distal sides. The practitioner can elect to add the second adhesive material 18*f* to the first adhesive material 15*f* when desired by pushing the appliance 14*f* in a downward direction. If the support 20*f* is made of a flexible material, the support 20*f* may bend and remain in contact with the appliance 14*f* as the second adhesive material 18*f* is added to the first adhesive material 15*f*. Alternatively, if the support 20*f* is made of a more rigid material, the appliance 14*f* may be pushed through the slit or opening of the support 20*f* for contact with the second adhesive material 18*f*, and then withdrawn from the container 12*f* by pulling the appliance 14*f* back through the slit or opening while the support 20*f* essentially remains in the configuration shown in FIG. 13.

As yet another option, one or more sides of the support 20*f* are spaced from the adjacent sidewall of the container 12*f* and the opening in the support 20*f* resembles the opening of the support 20*a* shown in FIG. 7. As one example, the support 20*f* may be constructed in the shape of a bar or strip that extends across the chamber of the container 12*f*, and the support 20*f* may include a notch for supporting the appliance 14*f* in suspended relationship within the chamber. The appliance 14*f* may be detached from the support 20*f* when desired by sliding the appliance 14*f* in a lateral direction (i.e., in a horizontal direction and toward the opening of the notch). In this example, the second adhesive material 18*f* may be located on the bottom 24*f* directly below the suspended appliance 14*f* or laterally offset from the suspended appliance 14*f*. Other aspects and options for the assembly 10*f* are similar to the aspects and options described above in connection with the assemblies 10-10*e*.

All of the patents and patent applications mentioned above are hereby incorporated by reference. The foregoing description is intended to exemplify various aspects of the invention and variations are possible. For example, the embodiments shown in FIGS. 1-4, 6-7, 9-10 and 12-13 could include a container similar to the container 12*d* shown in FIG. 11. As another example, additional quantities of the monomers or curatives of the adhesive materials mentioned above may be provided in the containers, such as in pores of supports that are made of foam. Supports for the appliances may have configurations other than as shown. Moreover, the concepts set out herein may be used in connection with appliances that are provided in indirect bonding trays.

Furthermore, any of the adhesive materials described above may be provided as multilayer adhesives as set out, for example, in published U.S. Patent Application No. 2005/0136370 (Brennan et al.). As one example, a thin layer of an adhesive material containing adhesion promoters may be adjacent the base of the appliance, and the second layer (i.e., the layer directly adjacent the first layer) may comprise an adhesive material that is selected for certain viscosity, handling or strength characteristics.

A number of other variations are also possible. Consequently, the invention should not be deemed limited to the presently preferred embodiments described in detail above, but instead only by a fair scope of the claims that follow and their equivalents.

The invention claimed is:

1. A packaged orthodontic assembly comprising:
   a container with a chamber;
   an orthodontic appliance received in the chamber, the appliance including a base;
   a first orthodontic adhesive material extending across the base of the appliance;
   a release surface in the chamber; and
   a second orthodontic adhesive material received on the release surface, wherein the second orthodontic adhesive material is spaced in the chamber from the first orthodontic adhesive material and is exposed in facing relation to the first orthodontic adhesive material for selective contact with the first orthodontic adhesive material when desired.

2. A packaged orthodontic assembly according to claim 1 and including a support for supporting the appliance in the chamber, the support comprising a pair of arms extending toward each other, each of the arms having an outer end section, the outer end sections being spaced from each other to present a receptacle therebetween, and wherein the appliance is received in the receptacle.

3. A packaged orthodontic assembly according to claim 2 wherein the appliance includes an occlusal recess and a gingival recess, and wherein the end sections of the arms are received in the occlusal and gingival recesses respectively.

4. A packaged orthodontic assembly according to claim 2 wherein the support has an overall, generally "C"-shaped configuration.

5. A packaged orthodontic assembly according to claim 1 and including a support for supporting the appliance in the chamber, wherein the support is resilient.

6. A packaged orthodontic assembly according to claim 5 wherein the support comprises a foam material.

7. A packaged orthodontic assembly according to claim 1 wherein the container includes a cover, and wherein the appliance is located in a position adjacent the cover when the cover is closed.

8. A packaged orthodontic assembly according to claim 1 wherein the container includes a cover, and wherein the appliance is located between the second adhesive material and the cover.

9. A packaged orthodontic assembly according to claim 1 wherein the release surface comprises a polymeric foam material.

10. A packaged orthodontic assembly according to claim 1 and including a support for supporting the appliance in the chamber, wherein the container includes a cover that can be moved from a closed to an open position, and wherein the support has sufficient memory to move the appliance in a direction away from the release surface when the cover is moved to an open position.

11. A packaged orthodontic assembly according to claim 10 wherein the container has a bottom, wherein the support has a longitudinal axis and is movable toward the bottom in a swinging manner, and wherein the bottom extends at an angle relative to the longitudinal axis.

12. A packaged orthodontic assembly according to claim 1 and including a third orthodontic adhesive material received in the chamber and spaced from the first orthodontic adhesive material and the second orthodontic adhesive material.

13. A packaged orthodontic assembly according to claim 1 and including a positioning member releasably connected to the orthodontic appliance, and wherein the positioning member at least partially supports the appliance in the chamber.

14. A packaged orthodontic assembly according to claim 1 wherein the second adhesive material includes a material that etches tooth enamel.

15. A packaged orthodontic assembly according to claim 1 wherein the second adhesive material includes a photobleachable dye.

16. A packaged orthodontic assembly according to claim 1 wherein the second adhesive material is at least partially cross-linkable to the first adhesive material once the second adhesive material contacts the first adhesive material.

17. A packaged orthodontic appliance according to claim 1 and including a support for supporting the appliance in the chamber, and wherein the support includes a section that represents the release surface.

18. A method of applying orthodontic adhesive material to an orthodontic appliance comprising:
   obtaining the packaged orthodontic assembly of claim 1;
   opening a cover of the container to expose the appliance; and
   relatively moving the appliance and the second orthodontic adhesive material in the chamber in order to bring the first adhesive material into contact with the second adhesive material.

19. A method of applying orthodontic adhesive material to an orthodontic appliance according to claim 18 wherein the act of opening the cover is carried out before the act of relatively moving the appliance and the second orthodontic adhesive material.

20. A method of applying orthodontic adhesive material to an orthodontic appliance according to claim 18 wherein the act of relatively moving the appliance and the second orthodontic adhesive material is carried out by pushing on the appliance.

21. A method of applying orthodontic adhesive material to an orthodontic appliance according to claim 20 wherein the act of relatively moving the appliance and the second orthodontic adhesive material is carried out by pushing on the appliance in a downward direction.

22. A method of applying orthodontic adhesive material to an orthodontic appliance according to claim 18 wherein the act of opening the cover enables the appliance to move in a direction away from the second orthodontic adhesive material.

23. A method of applying orthodontic adhesive material to an orthodontic appliance according to claim 18 wherein the first orthodontic material has a composition substantially identical to the composition of the second orthodontic material.

24. A method of applying orthodontic adhesive material to an orthodontic appliance according to claim 18 wherein the first orthodontic adhesive material has a viscosity that is greater than the viscosity of the second orthodontic adhesive material.

25. A method of applying orthodontic adhesive material to an orthodontic appliance according to claim 18 wherein the second orthodontic adhesive material comprises a primer for the first orthodontic adhesive material.

26. A method of applying orthodontic adhesive material to an orthodontic appliance according to claim 18 wherein the second orthodontic adhesive material comprises one or more of the following: a photobleachable dye and a material that etches tooth enamel.

27. A method of applying orthodontic adhesive material to an orthodontic appliance according to claim 18 wherein the second orthodontic adhesive material comprises one or more of the following components in a concentration by weight greater than any concentration by weight of the same component in the first orthodontic adhesive material: resin, solvent, photoinitiator, filler and dye.

* * * * *